United States Patent
Whitehurst et al.

(10) Patent No.: US 6,733,485 B1
(45) Date of Patent: May 11, 2004

(54) MICROSTIMULATOR-BASED ELECTROCHEMOTHERAPY METHODS AND SYSTEMS

(75) Inventors: Todd K. Whitehurst, Frazier Park, CA (US); James P. McGivern, Stevenson Ranch, CA (US); Matthew I. Haller, Valley Village, CA (US); Janusz A. Kuzma, Parker, CO (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 10/133,770

(22) Filed: Apr. 26, 2002

Related U.S. Application Data
(60) Provisional application No. 60/293,811, filed on May 25, 2001.

(51) Int. Cl.$^7$ .............................................. A61M 31/00
(52) U.S. Cl. ...................... 604/500; 604/891.1; 604/20; 607/120
(58) Field of Search ............... 604/20, 890.1, 604/891.1, 500; 607/120, 901

(56) References Cited

U.S. PATENT DOCUMENTS

| | | |
|---|---|---|
| 5,019,034 A | 5/1991 | Weaver et al. |
| 5,122,345 A | 6/1992 | Tabor et al. |
| 5,193,539 A | 3/1993 | Schulman et al. |
| 5,193,540 A | 3/1993 | Schulman et al. |
| 5,279,543 A | 1/1994 | Glikfeld et al. |
| 5,312,439 A | 5/1994 | Loeb |
| 5,389,069 A | 2/1995 | Weaver |
| 5,547,467 A | 8/1996 | Pliquett et al. |
| 5,869,326 A | 2/1999 | Hofmann |
| 5,983,131 A | 11/1999 | Weaver et al. |
| 6,010,613 A | 1/2000 | Walters et al. |
| 6,014,584 A | 1/2000 | Hofmann et al. |
| 6,021,347 A | 2/2000 | Herbst et al. |
| 6,022,316 A | 2/2000 | Eppstein et al. |
| 6,051,017 A | 4/2000 | Loeb et al. |
| 6,055,453 A | 4/2000 | Hofmann et al. |
| 6,085,115 A | 7/2000 | Weaver et al. |
| 6,103,084 A | 8/2000 | Uhen |
| 6,110,161 A | 8/2000 | Mathiesen et al. |

(List continued on next page.)

FOREIGN PATENT DOCUMENTS

| | | |
|---|---|---|
| WO | WO-98/43700 A1 | 10/1998 |
| WO | WO-98/43701 A1 | 10/1998 |

OTHER PUBLICATIONS

Belehradek, et al., "Electrochemotherapy, a New Antitumor treatment. First Clinical Phase I–II trial", Cancer, vol. 72(12), (Dec. 15, 1993), pp. 3694–3700.

Berendson, et al., "Electrochemical Aspects of Treatment of Tissue with Direct Current", European Journal of Surgery, Suppl. 574, (1994), pp. 111–115.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

(List continued on next page.)

*Primary Examiner*—LoAn H. Thanh
*Assistant Examiner*—Jeremy Thissell
(74) *Attorney, Agent, or Firm*—Laura Haburay Bishop

(57) ABSTRACT

A small implantable stimulator(s) includes at least two electrodes for delivering electrical stimulation to surrounding tissue and/or a pump and at least one outlet for delivering a drug or drugs to surrounding tissue. One electrochemotherapy method disclosed includes delivery of electrical stimulation in the form of a direct electric current and/or a periodic waveform that locally potentiates the cytotoxic effects of a systemically and/or locally administered chemotherapy agent(s). Open- and closed-loop systems are disclosed.

20 Claims, 8 Drawing Sheets

U.S. PATENT DOCUMENTS

| | | | |
|---|---|---|---|
| 6,164,284 | A | 12/2000 | Schulman et al. |
| 6,185,452 | B1 | 2/2001 | Schulman et al. |
| 6,208,894 | B1 | 3/2001 | Schulman et al. |
| 6,226,554 | B1 | 5/2001 | Tu et al. |
| 6,464,687 | B1 | 10/2002 | Ishikawa et al. |
| 6,472,991 | B1 | 10/2002 | Schulman et al. |
| 2002/0193859 | A1 | 12/2002 | Schulman et al. |

OTHER PUBLICATIONS

Cemazar, et al., "Intratumoral Cisplatin Administration in Electrochemotherapy: Antitumor Effectiveness, Sequence Dependence and Platinum Content", Anticancer Drugs, vol. 9(6), (Jul. 1998), pp. 525–530.

Domenge, et al., "Antitumor Electrochemotherapy: New Advances in the Clinical Protocol", Cancer, vol. 77(5), (Mar. 1, 1996), pp. 956–963.

Heller, et al., "Treatment of Cutaneous and Subcutaneous Tumors with Electrochemotherapy Using Intralesional Bleamycin", Cancer, vol. 83(1), (Jul. 1, 1998), pp. 148–157.

Horikoshi, et al., "Enhancing Effect of Electric Stimulation on Cytotoxicity of Anticancer Agents Against Rat and Human Glioma Cells", Brain Research Bulletin, vol. 51(5), (Mar. 15, 2000), pp. 371–378.

Hyacinthe, et al., "Electrically Enhancing Drug Delivery for the Treatment of Soft Tissue Sarcoma", Cancer, vol. 85(2), (Jan. 15, 1999), pp. 409–417.

Jaroszeski, et al., "Toxicity of Anticancer Agents Mediated by Electroporation in Vitro", Anticancer Drugs, vol. 11(3), (Mar. 2000), pp. 201–208.

Jaroszeski, "Electrically Mediated Drug Delivery for Treating Subcutaneous and Orthotopic Pancreatic Adenocarcinoma in a Hamster Model", Anticancer Res, vol. 19(2A), (Mar.–Apr. 1999), pp. 989–994.

Jaroszeski, et al., "In Vivo Antitumor Effects of Electrochemotherapy in a Hapatoma Model", Biochim Biophys Acta, vol. 1334(1), (Feb. 1997), pp. 15–18.

Kuriyama, et al., "Electrochemotherapy can Eradicate Established Colorectal Carcinoma and Leaves a Systemic Protective Memory in Mice", Int J Oncol, vol. 16(5), (May 2000), 979–985.

Kuriyama, et al., "Electrochemotherapy for Colorectal Cancer with Commonly Used Chemotherapeutic Agents in a Mouse Model", Dig Dis Sci, vol. 45(8), (Aug. 2000), pp. 1568–1577.

Maeda, et al., "Electrochemotherapy Potentiation of Antitumor Effect of Cyclophosphamide by Local Electric Pulses on the Metastatic Lesion of Hamster Oral Fibrosarcoma." printed Mar. 13, 2003, 10 pages.

Mir, et al., "Mechanisms of Electrochemotherapy", Adv Drug Deliv Rev, vol. 35(1), (Jan. 4, 1999), pp. 107–118.

Mitoro, et al., "Electrochemotherapy with Bleomycin Against Colorectal Carcinoma in a Mouse Model: Evaluations of the Dose and Administration Route of the Drug and the Electric Field Intensity", International Journal of Oncology, vol. 16(1), (Jan. 2000), pp. 97–104.

Sauer, et al., "Increased Doxorubicin Uptake and Toxicity in Multicellular Tumour Spheroids Treated with DC Electrical Fields", British Journal of Cancer, vol. 80(8), (Jun. 1999), pp. 1204–1213.

Sersa, et al., "Electrochemotherapy with Bleomycin in the Treatment of Hypernephroma Metastasis: Case Report and Literature Review", Tumori, vol. 86(2), (Mar.–Apr. 2000), pp. 163–165.

Sersa, et al., "Electrochemotherapy with Cisplatin: the Systemic Antitumour Effectiveness of Cisplatin Can Be Potentiated Locally by the Application of Electric Pulses in the Treatment of Malignant Melanoma Skin Metastases", Melanoma Research, vol. 10(4), (Aug. 2000), pp. 381–385.

Sersa, et al., "Potentiation of Bleomycin Antitumor Effectiveness by Electrotherapy", Cancer Lett, vol. 69(2), (Apr. 30, 1993), pp. 81–84.

Shi, et al., "Clinical Evaluation of Several Tumor Markers in the Diagnosis of Primary Heptic Cancer", Zhonghua Zhong Liu Za Zhi, 20(6) (Nov. 1998), pp. 437–439.

Taylor, et al., "Ablation of Neoplasia by Direct Current", British Journal of Cancer, vol. 70(2), (Aug. 1994), pp. 342–345.

Yen, et al., "Electrochemical Treatment of Human KB Cells in Vitro", Journal Bioelectromagnetics, vol. 20(1), (1999), pp. 24–41.

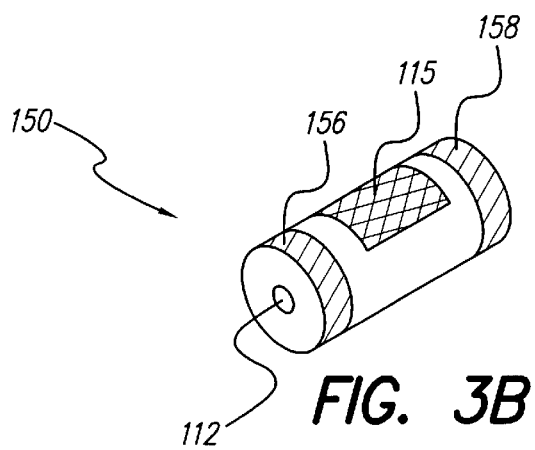
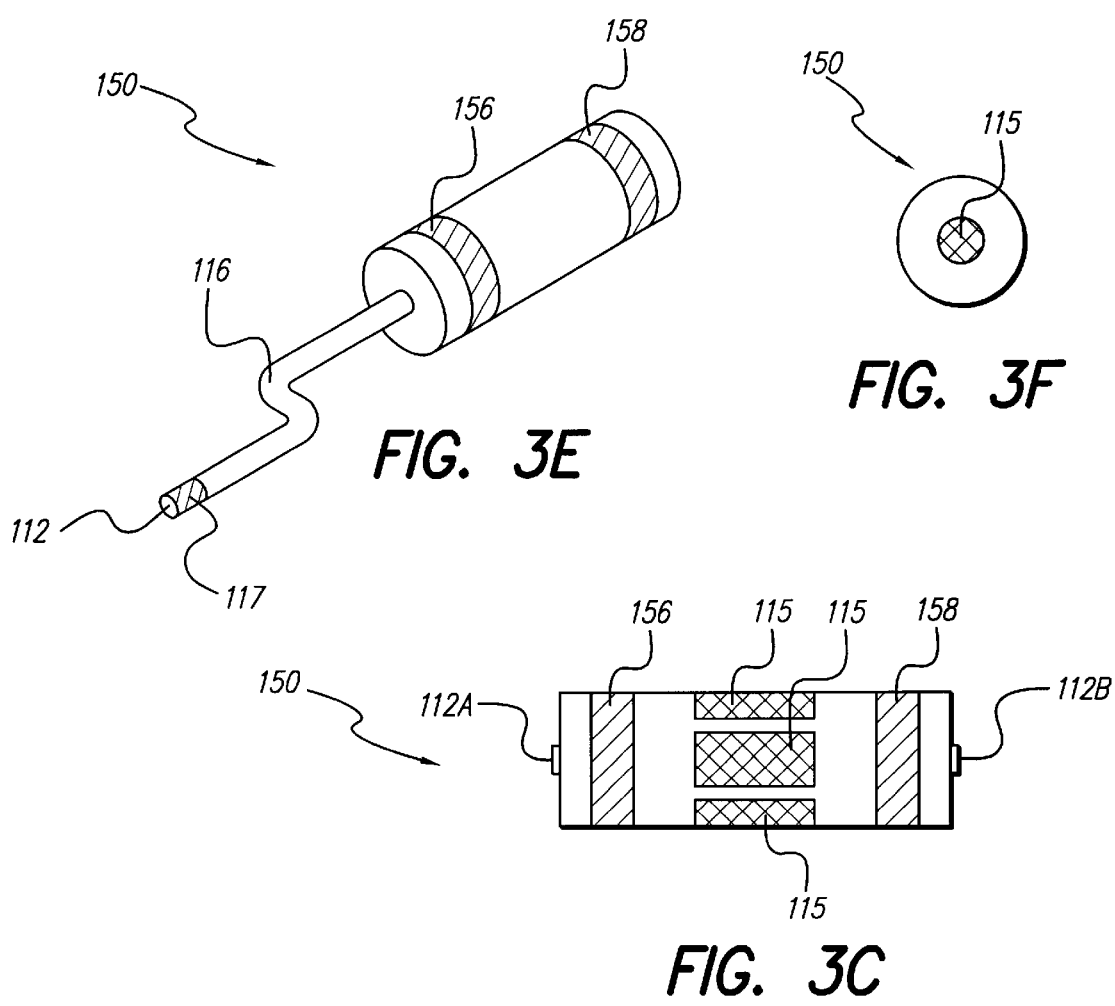

MICROSTIMULATOR-BASED ELECTROCHEMOTHERAPY METHODS AND SYSTEMS

The present application claims the benefit of U.S. Provisional Patent Application Serial No. 60/293,811, filed May 25, 2001, which application is incorporated herein by reference in its entirety.

FIELD OF THE INVENTION

The present invention generally relates to implantable drug delivery and electrical stimulation systems and methods, and more particularly relates to utilizing one or more implantable microstimulators for direct electrical current or electrical current pulses along with administration of a specific chemotherapy agent as a therapy for cancer and other neoplastic diseases.

BACKGROUND OF THE INVENTION

In the year 2000, an estimated 1,220,100 people in the United States were diagnosed with cancer and 552,200 died of this disease. Cancer is actually a group of many related diseases, but all cancers begin with an abnormal cell. The body is made up of many types of cells. Normally, cells grow and divide to produce more cells only when the body needs them. Sometimes, however, cells keep dividing when new cells are not needed. These extra cells form a mass of tissue, called a tumor, or a neoplasm. Tumors may be benign or malignant.

1. Benign tumors are not cancer. They can often be removed and usually do not come back. Cells from benign tumors do not spread to other parts of the body. Most importantly, benign tumors are rarely a threat to life.
2. Malignant tumors are cancer. Cells in these tumors are abnormal and divide without control or order. They can invade and damage nearby tissues and organs. Also, cancer cells can break away from a malignant tumor and enter the bloodstream or the lymphatic system. That is the most common way cancer spreads from the original cancer site to form new tumors in other organs. The spread of cancer is called metastasis.
3. Leukemia and lymphoma are cancers that arise in blood-forming cells. The abnormal cells circulate in the bloodstream and lymphatic system. They may also invade or infiltrate body organs and form tumors.

Most cancers are named for the organ or type of cell in which they begin. For example, cancer that begins in the lung is lung cancer, and cancer that begins in cells in the skin known as melanocytes is called melanoma.

When cancer spreads (i.e., metastasizes), cancer cells are often found in nearby or regional lymph nodes. If the cancer has reached these nodes, then cancer cells may have spread to other organs, such as the liver, bones, or brain. When cancer spreads from its original location to another part of the body, the new tumor has the same kind of abnormal cells and the same name as the primary tumor. For example, if lung cancer spreads to the brain, the cancer cells in the brain are actually lung cancer cells. The disease is called metastatic lung cancer.

Cancer Statistics

In men, lung cancer incidence rates have reached an apparent plateau, but prostate cancer has increased dramatically. As a result, cancer of the prostate gland has become the most common type of cancer among both black (incidence rate of 163.1 per 100,000) and white (121.2 per 100,000) males. Lung cancer and colorectal cancer rates are the second and third highest, respectively, for both black and white males.

Breast cancer is by far the most common cancer among both white and black females. It occurs more frequently among white females (113.2 per 100,000) than among black females (94.0 per 100,000). Lung cancer and colorectal cancer are the second and third highest cancers, respectively, among white females compared to ranks of third and second highest, respectively, for black females. Even though lung and colorectal cancers are two of the most common cancers among females, their incidence is much lower than that for males. The fourth most common cancer for both white and black females is uterine cancer.

Treatment

Treatment for cancer can be either local or systemic. Local treatments affect cancer cells in the tumor and the area near it. Systemic treatments travel through the bloodstream, reaching cancer cells all over the body. Surgery and radiation therapy are types of local treatment. Chemotherapy, hormone therapy, and biological therapy are examples of systemic treatment. Healthy cells generally also suffer from the harmful effects of cancer treatment, which may lead to significant side effects.

Surgery includes removal of the cancer and typically some of the surrounding tissue and lymph nodes near the tumor. The side effects of surgery depend on many factors, including the size and location of the tumor, the type of operation, and the patient's general health.

Radiation therapy (a.k.a. radiotherapy) may be used instead of surgery as the primary treatment for some types of cancer. It also may be given before surgery (a.k.a., neoadjuvant therapy) to shrink a tumor so that it is easier to remove. In other cases, radiation therapy is given after surgery (a.k.a., adjuvant therapy) to destroy any cancer cells that may remain in the area. In addition, radiation may be used alone, or along with other types of treatment, to relieve pain or other problems if the tumor cannot be removed. Radiation therapy can be in either of two forms: external or internal, and some patients receive both.

External radiation comes from a machine that aims the rays at a specific area of the body, and there is no radioactivity left in the body after the treatment.

With internal radiation (also called implant radiation, interstitial radiation, or brachytherapy), the radiation comes from radioactive material in needles, seeds, wires, or catheters and placed directly in or near the tumor. Patients may stay in the hospital while the level of radiation is highest. During the hospital stay, patients may not be able to have visitors or may have only short visits, because patients may be immunocompromised and prone to infection, and because visitors may be exposed to radiation. Implants may be permanent or temporary. The amount of radiation in a permanent implant goes down to a safe level before the person leaves the hospital. The doctor will advise the patient if any special precautions should be taken at home (e.g., avoiding people with infections, care of an implant wound site). With a temporary implant, there is no radioactivity left in the body after the implant is removed.

The side effects of radiation therapy depend on the treatment dose and the part of the body that is treated. Patients are likely to become extremely tired during radiation therapy, especially in the later weeks of treatment. Radiation therapy also may cause a decrease in the number of white blood cells, which are the cells that help protect the body against infection. With external radiation, there may be permanent darkening or "bronzing" of the skin in the treated area. In addition, it is common to have temporary hair loss in the treated area, and for the skin to become red, dry, tender, and itchy.

Chemotherapy is the use of drugs to kill cancer cells. One drug or a combination of chemotherapy agents may be used. Chemotherapy may be the only kind of treatment a patient needs, or it may be combined with other forms of treatment. Neoadjuvant chemotherapy refers to drugs given before surgery to shrink a tumor; adjuvant chemotherapy refers to drugs given after surgery to help prevent the cancer from recurring. Chemotherapy also may be used (alone or along with other forms of treatment) to relieve symptoms of the disease.

Chemotherapy is usually given in cycles: a treatment period (one or more days when treatment is given) followed by a recovery period (several days or weeks), then another treatment period, and so on. Most anticancer drugs are given intravenously, some are injected intramuscularly or subcutaneously, and some are given by mouth.

Sometimes the chemotherapy agents are given in other ways. For example, in an approach called intraperitoneal chemotherapy, chemotherapy agents are placed directly into the abdomen through a catheter. To reach cancer cells in the central nervous system (CNS), the patient may receive intrathecal chemotherapy, in which the chemotherapy agents enter the cerebrospinal fluid through a needle placed in the spinal column, or through a device placed under the scalp.

The side effects of chemotherapy depend mainly on the drugs and the doses the patient receives. As with other types of treatment, side effects vary from person to person. Generally, chemotherapy agents affect cells that divide rapidly. In addition to cancer cells, these include red blood cells and white blood cells. When blood cells are affected, patients are more likely to get infections, may bruise or bleed easily, and may feel unusually weak and very tired. Rapidly dividing cells in hair roots and cells that line the digestive tract may also be affected. As a result, side effects may include loss of hair, poor appetite, nausea and vomiting, diarrhea, or mouth sores. Some chemotherapy agents only cause the hair to thin, while others may result in the loss of all body hair. Most side effects go away gradually during the recovery periods between treatments, and hair grows back after treatment is over. Some chemotherapy agents can cause long-term side effects such as loss of fertility.

Hormone therapy is used against certain cancers that depend on hormones for their growth, such as certain types of breast cancer and prostate cancer. Hormone therapy typically consists of drugs that are antagonists to the hormone needed to sustain the growth of the cancer cells, but this treatment may also include the use of drugs that decrease the production or enzymatic conversion of certain hormones. Another type of hormone therapy is surgery to remove organs (such as the ovaries or testicles) that make hormones.

Hormone therapy can cause a number of side effects. Patients may feel tired, have fluid retention, weight gain, hot flashes, nausea and vomiting, changes in appetite, and, in some cases, blood clots. In women, hormone therapy may cause interrupted menstrual periods and vaginal dryness. Hormone therapy in women may also cause either a loss of or an increase in fertility. In men, hormone therapy may cause erectile dysfunction, loss of sexual desire, or loss of fertility. Depending on the drug used, these changes may be temporary, long-lasting, or permanent.

Biological therapy (also called immunotherapy) helps the body's own immune system to fight cancer or to protect the body from some of the side effects of cancer treatment. Some examples of biological therapy include monoclonal antibodies, interferon (IFN), interleukin-2 (IL-2), and colony-stimulating factors (e.g., G-CSF).

The side effects caused by biological therapy vary with the specific treatment. In general, these treatments tend to cause flu-like symptoms, such as chills, fever, muscle aches, weakness, loss of appetite, nausea, vomiting, and diarrhea. Patients also may bleed or bruise easily, get a skin rash, or have swelling. These problems can be severe, but they go away after the treatment stops.

Drawbacks of available cancer treatments include damage to healthy cells and the resulting significant side effects, such as fatigue, hair loss, hormonal changes that may affect fertility and desire, blood clots, and flu-like symptoms, and/or complex, risky, expensive surgical procedures. What is needed is a therapy for patients with cancer and other neoplastic diseases that is minimally invasive, and provides effective treatment without major side effects.

BRIEF SUMMARY OF THE INVENTION

The invention disclosed and claimed herein addresses the above and other needs and provides implantable, minimally invasive systems and methods for chronically stimulating malignant tumors and other neoplasms with direct electrical current or electrical current pulses, along with administration of a chemotherapy agent(s). Administration of such electrochemotherapy stimulation may provide significant therapeutic benefits in the treatment, control, and/or prevention of cancer and other neoplastic diseases through one or more of a variety of mechanisms discussed below.

A miniature implantable electrical stimulator, such as a Bionic Neuron (also referred to as a BION® microstimulator) or the like, is provided to treat, via electrochemotherapy, neoplastic diseases such as cancer. The microstimulator may be implanted in a neoplasm via a minimal surgical procedure (e.g., via a small incision and through a cannula, endoscopically, etc.). When synchronized with the administration of a specific chemotherapy agent(s), pulses of electric current and/or a direct electric current will likely be effective in fighting cancer (e.g., by inducing localized necrosis of neoplastic tissue).

The implantable stimulator capable of supplying direct current (DC), electric current pulses, and/or drug infusion used with the present invention possesses one or more of the following properties, among other properties:

- at least two electrodes for applying electrical stimulation to surrounding tissue and/or a pump and at least one outlet for delivering a drug or drugs to surrounding tissue;
- electronic and/or mechanical components encapsulated in a hermetic package made from biocompatible material(s);
- an electrical coil or the like for receiving energy and/or information inside the package, which receives power and/or data by, for instance, inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the microstimulator; and
- a form factor making the microstimulator implantable via a minimal surgical procedure in a target area in the body.

The length and shape of the microstimulator may be varied in order to deliver more effective treatment, e.g., to treat neoplasms of different shapes and sizes. For example, the microstimulator may be a thin cylindrical device with an electrode at each end, or may be a cylindrical device with multiple electrodes along its length and/or circumference, or may be a flat circular device with two or more electrodes distributed around its periphery, or may be a spherical device with two or more electrodes distributed on its surface, or may have any size and configuration suitable for the particular treatment location and stimulation/infusion parameters.

A microstimulator may operate independently, or in a coordinated manner with other implanted microstimulators, other implanted devices, or with devices external to the patient's body. For instance, a microstimulator may incorporate sensor(s) for sensing a patient's condition, which information may be used to control electrical and/or drug stimulation parameters in a closed loop manner. The sensing and electrical stimulation capabilities may be incorporated into a single microstimulator; the sensing and drug stimulation capabilities may be incorporated into a single microstimulator; and/or the sensing, electrical stimulation, and drug stimulation capabilities may all be incorporated into a single microstimulator. Alternatively or additionally, a sensor(s) may communicate sensed information to at least one microstimulator with stimulation capabilities, i.e., that can supply a direct electric current and/or electric current pulses, and/or drug infusion.

BRIEF DESCRIPTION OF THE SEVERAL VIEWS OF THE DRAWINGS

The above and other aspects of the present invention will be more apparent from the following more particular description thereof, presented in conjunction with the following drawings wherein:

FIG. 3B is a perspective view of a microstimulator made in accordance with certain embodiments of the invention;

FIG. 3C is a side view of an alternative configuration of a microstimulator;

FIG. 3E is a perspective view of still another configuration of a microstimulator;

FIG. 3F is a view of one end of the stimulator of FIG. 3E;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
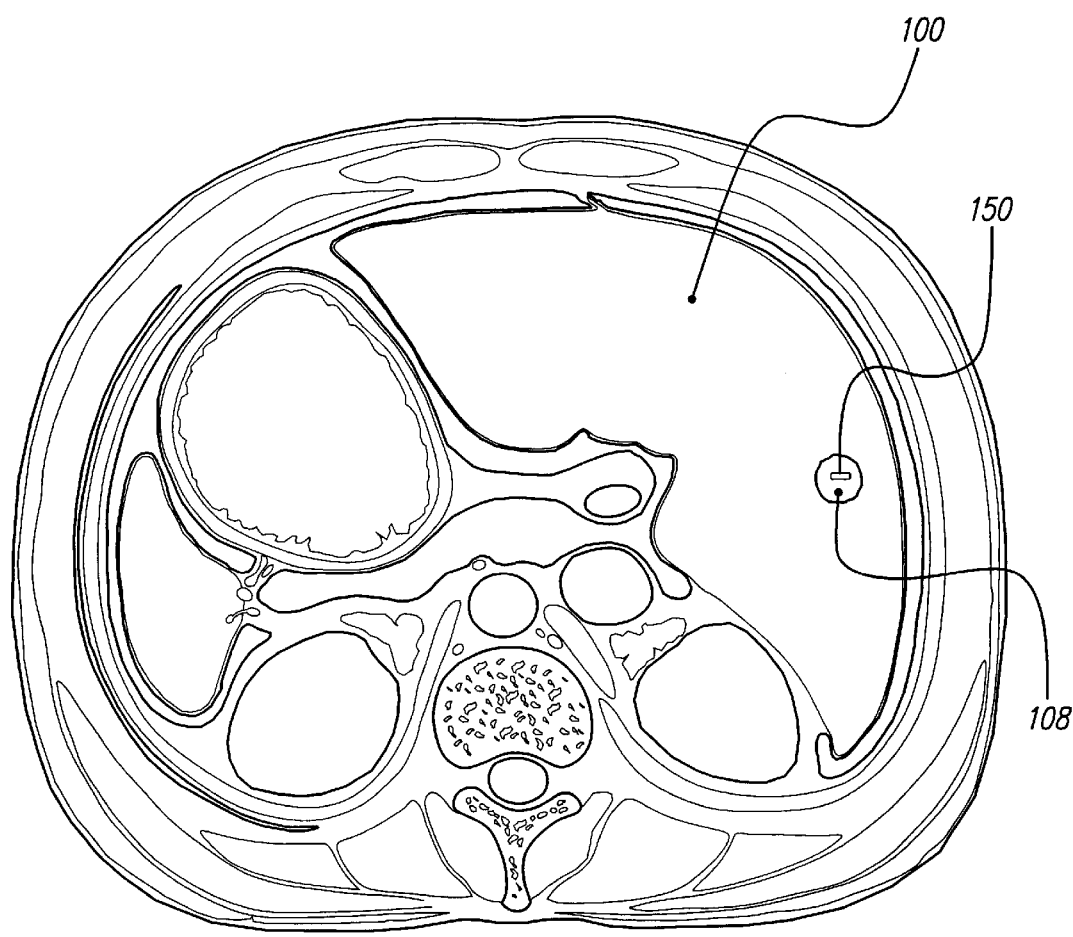
FIG. 1 is a transverse cross-section, at the level of the T12 vertebra, of the abdomen and viscera, including the liver.
Figure 2:
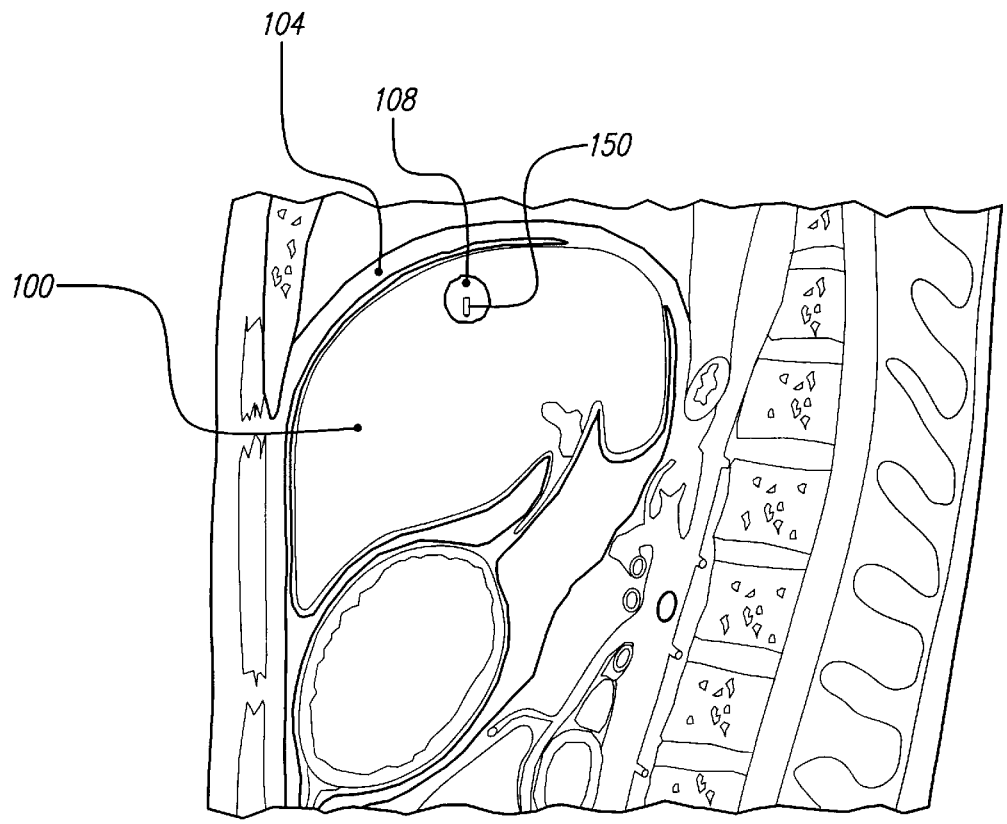
FIG. 2 is a sagittal cross-section view of the abdomen and viscera.

FIGS. 1 and 2 show a transverse cross-section view and a sagittal cross-section view, respectively, of the abdomen and viscera, including the liver. As can be seen, the liver 100 occupies the upper, right portion of the abdominal cavity, immediately below the diaphragm 104. A tumor or neoplasm 108 is depicted within liver 100. Liver 100 and liver tumor 108 of FIGS. 1 and 2 will be used to demonstrate the present invention.

Electrochemotherapy

As described above, chemotherapy is a common therapy for cancer. Electrical stimulation, e.g., using low-level direct current (DC) stimulation, has also been investigated as a means of therapy for neoplasms. While these two methods are each effective in fighting cancer alone, the combination of the two, known as electrochemotherapy, electropermeabilization, or electroporation, may prove to be a more powerful weapon against cancer and other neoplastic diseases.

Mechanism of Action

The mechanism of action of electrochemotherapy is essentially unknown. It has been hypothesized that electrical stimulation, such as short and intense locally-applied electric pulses, creates micropores in the cell membrane of cancer cells (as well as other local cells). According to the hypothesis, these micropores allow chemotherapy agents to enter the interior of the cell (i.e., the cytoplasm). Chemotherapy agents must enter cells in order to exert their toxic effects, but some cancer cells may resist chemotherapy agents by blocking their entry or by actively pumping them out. Electrochemotherapy may thus allow more effective treatment of non-resistant cancers as well as improved therapy of treatment-resistant cancers.

Other evidence suggests that cell membrane permeability is not the mechanism of action of electrochemotherapy. In 1999, Sauer, et al. treated multicellular prostate tumor spheroids with non-lethal DC electrical fields, along with administration of doxorubicin ("Increased doxorubicin uptake and toxicity in multicellular tumour spheroids treated with DC electrical fields". British Journal of Cancer, June 1999, 80(8):1204–13). (Doxorubicin is a common chemotherapy agent that is discussed in more detail below.) An electrical field with field strength of 500 V/m was applied for a duration of 90 seconds. The treated spheroids did not experience membrane breakdown, but did increase their uptake of doxorubicin. The electrical field raised intracellular reactive oxygen species, which induced membrane lipid peroxidation, which, in turn, decreased lipid diffusion significantly. The electric field effects were mimicked by incubating spheroids with hydrogen peroxide and were inhibited by the radical scavengers dehydroascorbate (DHA) and alpha-tocopherol (vitamin E), indicating that the increased uptake of doxorubicin after electrical field treatment is likely due to lipid peroxidation and the associated decrease in membrane lipid mobility.

Supporting the hypothesis that reactive chemical species may be responsible for the potentiating effects of electrical stimulation in electrochemotherapy, a 1994 study described the primary reactions in the electrochemical treatment of tissue with direct electric current (Berendson, et al. "Electrochemical aspects of treatment of tissue with direct current" European Journal of Surgery, Suppl., 1994; (574):111–5). The main reactions at the anode are the formation of oxygen, acidification due to liberated hydrogen ions, and, if platinum is used as anode material, the formation of chloride. At the cathode, hydrogen is formed and hydroxide ions are liberated. Based on calculations, the authors concluded that the liberated hydrogen ions determine the extents of the locally destroyed zone around the anode and that the destructive effect of chlorine probably occurs in an inner zone close to the anode.

Chemotherapy Agents

Electrochemotherapy has been investigated with several chemotherapy agents, including bleomycin, doxorubicin, cisplatin, and cyclophosphamide.

Bleomycin has been most widely investigated for electrochemotherapy. Bleomycin destroys rapidly dividing cells by causing DNA fragmentation, and inhibits cell proliferation by inhibiting DNA synthesis. In an in vitro study, it was found that the dose of bleomycin can be reduced by a factor of 100–5000 when administered along with electrical stimulation. Systemically administered bleomycin does not significantly suppress production of blood cells (a.k.a. myelosuppression) relative to other chemotherapy agents; however, it can lead to severe fibrosis (i.e., scarring) of the lungs and skin. Bleomycin is typically used in the treatment of Hodgkin's disease and other lymphomas. It is also used in the treatment of testicular cancer, head and neck sarcomas, and Kaposi's sarcoma, a common affliction of AIDS patients.

In early work on electrochemotherapy, Belehradek, et al. studied eight patients with 40 permeation nodules of head and neck squamous cell carcinomas ("Electrochemotherapy, a new antitumor treatment. First clinical phase I–II trial". Cancer, Dec. 15, 1993; 72(12):3694–700). The patients were treated with a 10 mg/m² bleomycin intravenous bolus, followed by four or eight cycles of 100 μsec pulses at 1300 V/cm administered through two external electrodes located on each side of the treated nodule. Neither local nor general side effects were observed, and electrochemotherapy was well tolerated. In addition, local antitumor efficacy was clearly demonstrated: 23 nodules (57%) had a clinical complete response within a few days.

In a 1996 study, Domenge, et al. tested various protocols of electrochemotherapy in the treatment of seven patients, each with a different type of cancer, including head and neck squamous cell carcinoma (HNSCC) permeation nodules, salivary cancer, and breast cancer ("Antitumor electrochemotherapy: new advances in the clinical protocol." Cancer, Mar. 1, 1996;77(5):956–63). The applied waveform was four or eight cycles of 100 μsec pulses at 1000 or 1300 V/cm. The therapeutic window for electrical stimulation delivery was found to be between 8 and 28 minutes after bleomycin intravenous injection. The technique was also demonstrated to be effective after intraarterial or intranodular injection of bleomycin. Clear antitumor effects were obtained, especially in the small nodules, and extended tumor necrosis was observed in the largest nodules.

In an in vitro study of human T98G glioma cells, Horikoshi, et al. found that electric stimulation significantly enhanced the cytotoxicity of bleomycin ("Enhancing effect of electric stimulation on cytotoxicity of anticancer agents against rat and human glioma cells." Brain Research Bulletin, Mar. 15, 2000; 51(5):371–8). The applied waveform was eight cycles of a 1 Hz square wave with a pulse width of 100 μsecond and an electric field of 1000 V/cm. The toxicity of bleomycin was increased by more than 1000-fold. This increase disappeared when bleomycin concentration was reduced to 100 pg/ml.

In similar work, Heller, et al. combined bleomycin with six to eight cycles of a 1 Hz square wave with a pulse width of 100 msecond and an electric field of 1300 V/cm to treat cutaneous and subcutaneous tumors in 34 patients ("Treatment of cutaneous and subcutaneous tumors with electrochemotherapy using intralesional bleomycin" Cancer, Jul. 1, 1998; 83(1):148–57). All patients responded to the treatment. Responses were observed in 142 of 143 metastatic nodules or primary tumors within 12 weeks, with complete responses observed in 91% of the nodules. No complete responses were observed in nodules treated with bleomycin only or electric pulses only. All patients tolerated the procedure well, and no significant side effects were noted.

In 2000, Sersa, et al. treated a patient with metastasis of hypernephroma with bleomycin followed by local application of electric pulses ("Electrochemotherapy with bleomycin in the treatment of hypernephroma metastasis: case report and literature review" Tumori, March–April 2000; 86(2):163–5). Over four weeks, the subcutaneous metastasis of the hypernephroma was treated three times, each session consisting of 9–10 cycles of 8 electric pulses 10 minutes after intravenous injection of bleomycin. This treatment stabilized the tumor volume for 12 months, while an untreated subcutaneous metastasis beside the treated one progressed immediately.

Studies have also found that bleomycin-based electrochemotherapy may be effective for colorectal cancer. Mice with a subcutaneously established colorectal tumor were administered intratumorally, intravenously, or intraperitoneally with bleomycin ranging from ⅟₅₀ to ½ of the normal 50% lethal dose (Mitoro, et al., "Electrochemotherapy with bleomycin against colorectal carcinoma in a mouse model: evaluations of the dose and administration route of the drug and the electric field intensity" International Journal of Oncology, January 2000; 16(1):97–104). Significant suppression of tumor development and even some cures were observed. Electric field intensities ranging from 500 to 2,000 V/cm were applied; all treatment protocols were similarly effective. Furthermore, when electrochemotherapy with the lowest dose of bleomycin and the lowest electric field intensity was repeated, complete cures of colorectal cancer were achieved in all animals. Other studies in animals have suggested that bleomycin-based electrochemotherapy may be effective for other types of cancer, including pancreatic cancer and soft tissue sarcomas.

Doxorubicin (Adriamycin®) acts to inhibit DNA topoisomerase II, an enzyme critical to DNA replication and transcription. Its primary acute toxic side effect is a large decrease in white blood cells (and less commonly, red blood cells and platelets). Its primary chronic toxic side effect is cardiomyopathy and congestive heart failure. Doxorubicin is used to treat Hodgkin's disease and other non-Hodgkin's lymphomas; breast, bladder, liver, lung, and thyroid cancers; and bone and soft tissue sarcomas. Sauer, et al. performed a study of doxorubicin, the results of which are described above.

Cisplatin (Platinol®) has also been investigated for electrochemotherapy. It destroys rapidly dividing cells by crosslinking DNA strands and by crosslinking DNA with intracellular proteins. The binding of platinum to DNA is responsible for at least part of the toxic effects of cisplatin. Its primary toxic side effect is irreversible kidney damage (nephrotoxicity), which is cumulative and generally dose-limiting. Other side effects include intractable nausea and vomiting, neurotoxicity, and myelosuppression. An in vitro study found that the cytotoxic dose of cisplatin and carboplatin can be reduced by a factor of 3–13 when administered along with electrical stimulation (Jaroszeski, et al. "Toxicity of anticancer agents mediated by electroporation in vitro" Anticancer Drugs, March 2000; 11(3):201–8). Cisplatin is used to treat cancer of the testis, ovary, uterus, bladder, head, neck, and lung, and is also used for soft tissue and bone sarcomas and refractory non-Hodgkin's lymphomas.

Sersa, et al. compared cisplatin alone with cisplatin-based electrochemotherapy ("Electrochemotherapy with cisplatin: the systemic antitumour effectiveness of cisplatin can be potentiated locally by the application of electric pulses in the treatment of malignant melanoma skin metastases" Melanoma Research, August 2000; 10(4):381–5). The study included nine malignant melanoma patients with skin metastases and metastases in lymph nodes not amenable to surgery. Twenty seven skin tumor nodules were treated with electrochemotherapy, and 18 received only cisplatin. Four weeks after electrochemotherapy treatment, 48% of the tumor nodules had responded, compared with 22% of the tumor nodules treated with cisplatin alone. Furthermore, the median time to progression was 21 weeks in the electrochemotherapy-treated nodules, versus four weeks in the chemotherapy-treated nodules.

Cemazar, et al. performed a study using intratumoral cisplatin on tumors in mice ("Intratumoral cisplatin administration in electrochemotherapy: antitumor effectiveness, sequence dependence and platinum content" Anticancer Drugs, July 1998; 9(6):525–30). Mice were treated with eight electric pulses (100 $\mu$sec, 1 Hz, 1040 V) and/or cisplatin (1, 2, 4, and 8 mg/kg). Cisplatin treatment resulted in up to 20 days of tumor growth delay. Electrochemotherapy resulted in tumor cures; local tumor control reached a plateau at 4 mg/kg in 67% of tumor cures. The maximal effect was achieved when cisplatin was injected 5 minutes before or simultaneously with electric pulse application. Approximately two times more platinum was bound to DNA in electrochemotherapy than in cisplatin treated tumors at all time points tested.

Cyclophosphamide is a widely used chemotherapy and immunosuppressive agent. In 1998, Maeda, et al. studied the effect of electrical pulses applied to the tumor site several minutes after injection of cyclophosphamide ("Electrochemotherapy Potentiation of Antitumor Effect of Cyclophosphamide by Local Electric Pulses on the Metastatic Lesion of Hamster Oral Fibrosarcoma." Fifth Internet World Congress for Biomedical Sciences, Dec. 7–16, 1998; Cancer Poster Session). In the study, oral fibrosarcoma was transplanted into the cheek pouch of hamsters. After transplantation, the metastatic lesions appeared in the regional lymph nodes of the hamsters. When the tumor size in a metastatic lesion was approximately 100 mm$^3$, treatments were initiated. The animals with metastatic lesions received an intraperitoneal injection of cyclophosphamide followed by local delivery of electric pulses to the metastatic site. The tumor was markedly reduced in size several days after this treatment. Cyclophosphamide injection alone or electric pulse treatment alone had no significant suppressive effect on the tumor growth.

Other chemotherapy agents have proven less effective as part of an electrochemotherapy regimen. A study by Horikoshi, et al. found the cytotoxicity of carboplatin only slightly enhanced by electric stimulation when a high dose of carboplatin was used ("Enhancing effect of electric stimulation on cytotoxicity of anticancer agents against rat and human glioma cells." Brain Research Bulletin, Mar. 15, 2000; 51(5):371–8). They further report no electrochemotherapy enhancement of the cytotoxicity of nimustine hydrochloride (ACNU), etoposide, and vincristine.

Drawbacks of available cancer treatments include damage to healthy cells and the resulting significant side effects, such as fatigue, hair loss, hormonal changes that may affect fertility and desire, blood clots, and flu-like symptoms, and/or complex, risky, expensive surgical procedures. Recently, small, implantable microstimulators have been introduced that can be implanted into soft tissues via a minimal surgical procedure. What is needed and provided herein is a therapy for patients with cancer and other neoplastic diseases that uses such a device(s), that is minimally invasive, and provides effective treatment without major side effects.

In accordance with the teachings of the present invention and as discussed in more detail presently, direct electrical current or electrical current pulses, along with chemotherapy agents, delivered to a neoplasm 108 are provided to treat, control, and/or prevent cancer and other neoplastic diseases. As described earlier, neoplastic diseases involve one or more abnormal benign or malignant masses of tissue. The present invention is directed to providing treatment using one or more small, implantable stimulators, referred to herein as "microstimulators". As used herein, stimulation refers to supplying a direct electrical current, including a low-level direct electrical current, or electrical current pulses, and/or infusion of a chemotherapy agent or other stimulating drug. Herein, these drugs comprise chemotherapy agents, medications, immunotherapy agents, synthetic or natural hormones, hormone therapy agents, anesthetic agents, enzymes, neurotransmitters, ketones, electrolytes, interleukins, cytokines, lymphokines, chemokines, growth factors, other intracellular and intercellular chemical signals and messengers, and the like. A microstimulator is sometimes referred to herein as simply a stimulator, and electrical current parameters and/or infusion parameters are sometimes referred to herein as stimulation parameters.

The microstimulators of the present invention may be similar to or of the type referred to as BION® devices. The following documents describe various details associated with the manufacture, operation, and use of BION implantable microstimulators, and are all incorporated herein by reference:

| Application/Patent/ Publication No. | Filing/publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |

-continued

| Application/Patent/ Publication No. | Filing/publication Date | Title |
|---|---|---|
| PCT Publication WO 98/37926 | Published Sep. 3, 1996 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 | Issued Apr. 18, 2000 | Improved Implantable Microstimulator and Systems Employing Same |
|  | Published Sep., 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

As will be evident to those of ordinary skill in the art upon review of the present description and of the publications listed above, the direct current (DC) blocking capacitor normally present in the circuitry of BIONs used for neurostimulation applications is removed when it is desired that the BIONs produce DC current (where such current is at least a portion of the desired therapeutic modality), as in various embodiments of the present invention.

Figure 3A:
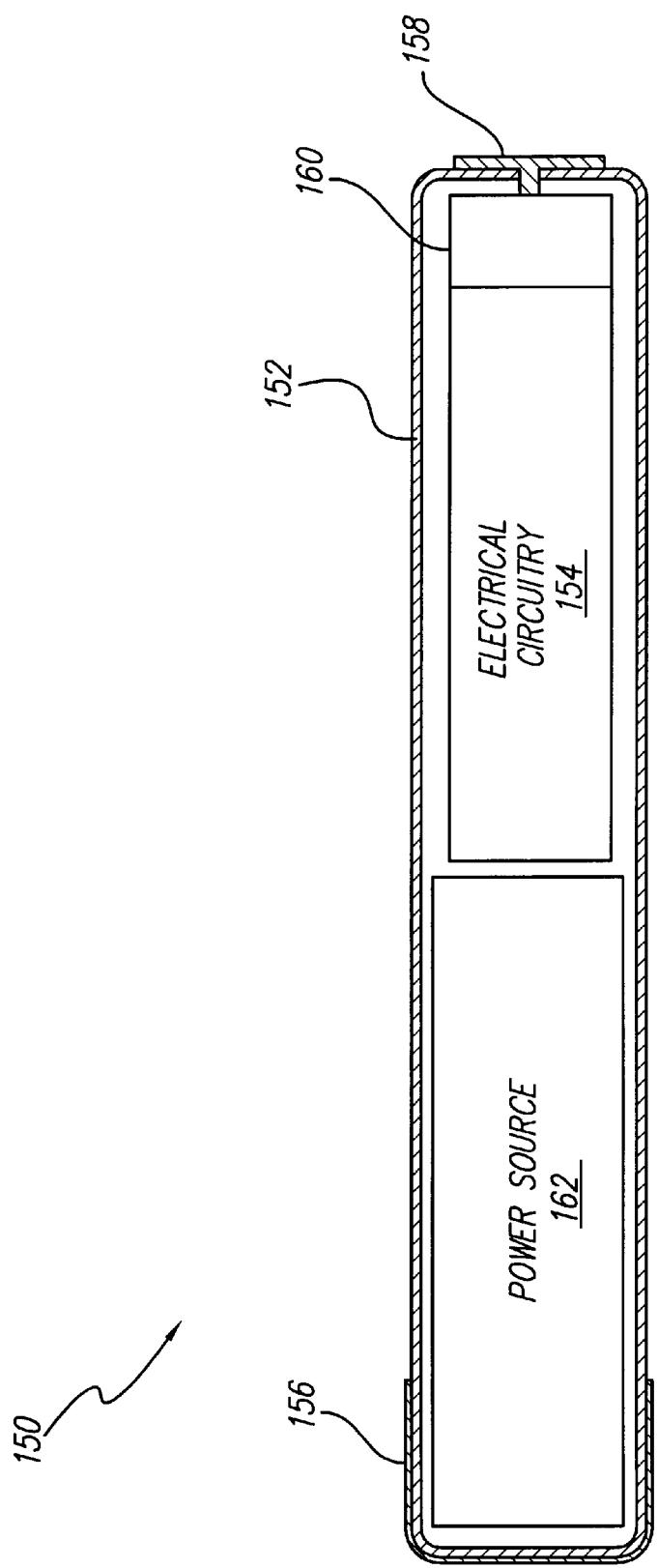
FIG. 3A is a side cross-sectional view of an exemplary embodiment of a stimulation system of the present invention.

As shown in FIG. 3A, microstimulator device 150 may include a narrow, elongated capsule 152 containing electrical circuitry 154 connected to electrodes 156 and 158, which may pass through the walls of the capsule at either end. Alternatively, electrodes 156 and/or 158 may be built into and/or onto the case and/or arranged on a catheter 116 (FIG. 3E) or at the distal portion of a lead, as described below. As detailed in the referenced publications, electrodes 156 and 158 generally comprise a stimulating electrode (to be placed close to the target tissue) and an indifferent electrode (for completing the circuit). Other configurations of device 150 are possible, as is evident from the above-referenced publications, and as described in more detail herein.

Certain configurations of implantable microstimulator 150 are sufficiently small to permit placement entirely within or near neoplasm 108. In accordance with the present invention, a single microstimulator 150 may be implanted, or two or more microstimulators may be implanted to achieve drug infusion, pulses of electric current, and/or direct electric current application to a larger region or for a longer period of time, as discussed in more detail presently.

In some such configurations, capsule 152 may have a diameter of about 4–5 mm, or only about 3 mm, or even less than about 3 mm. In these configurations, capsule length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIG. 3A, is one possible configuration, but other shapes, such as rounded cylinders, disks, spheres, and helical structures, are possible, as are different configurations of and/or additional electrodes, infusion outlets, leads, and/or catheters.

As mentioned earlier, "drug" comprises, among other things, chemotherapy agent(s), medication(s), immunotherapy agent(s), and hormone(s). As such, a microstimulator may also include infusion capabilities for delivering one or more chemotherapy agents, other medications, or other fluids. The infusion capabilities may include direct delivery of the drug(s) by the microstimulator (i.e., without a catheter), or it may alternatively include a small catheter that is attached to the microstimulator.

Electrical stimulation may take the form of a series or sequence of electrical pulses of a type typically used for, e.g., stimulation of nerve and muscle tissue. Alternatively, such electrical stimulation may take the form of very high-voltage electrical pulses. The stimulator may alternatively generate a DC or slowly varying waveform.

The stimulator may be configured so electrical stimulation operates in conjunction with drug infusion. Alternatively, the electrical stimulation may be provided as an alternative to the drug stimulation. In the latter case, and as described in more detail presently, at least two microstimulators may be implanted: one or more electrical stimulation microstimulators and one or more drug infusion microstimulators.

Examples of alternative configurations of stimulator 150 are illustrated in FIGS. 3B–3I, 4A, 4B, and 6, and are described below. Microstimulator 150 may have a single infusion outlet 112 (FIG. 3B), dual infusion outlet(s) 112A, 112B (FIG. 3C), or multiple infusion outlets 112C, 112D (e.g., FIGS. 3D and 3I) that is/are substantially flush with the device (i.e., the device does not include a catheter) for allowing fluid egress from the device. In other embodiments, such as shown in FIG. 3E, the infusion is provided through one or more catheters 116 having at least one infusion outlet 112 at a distal end and/or along a distal portion of the catheter(s). Additionally or alternatively, catheter(s) 116 may have one or more electrodes 117 at a distal end and/or along the distal portion of the catheter. In some configurations, fluid egress occurs by passing the fluid through a membrane or a filter near or part of an infusion outlet(s) and/or that is part of a catheter attached to the device.

A septum 115, or other membrane or device allowing transcutaneous refilling of a fluid by injection into an internal reservoir(s), may be located on the surface of microstimulator 150. A septum 115 (FIG. 3B) or multiple septa 115 (FIG. 3C) may be used, and may be square/rectangular (FIG. 3B), rounded (FIGS. 3D and 3I), at the end of the device (FIG. 3F), around the circumference of the device (FIGS. 3B–3D), or any other useful shape in any other useful location. Septum 115 may be punctured by a hypodermic needle (e.g., syringe) to allow transcutaneous filling of the fluid reservoir(s), while typically not allowing any significant leakage following such puncture.

Figure 3D:
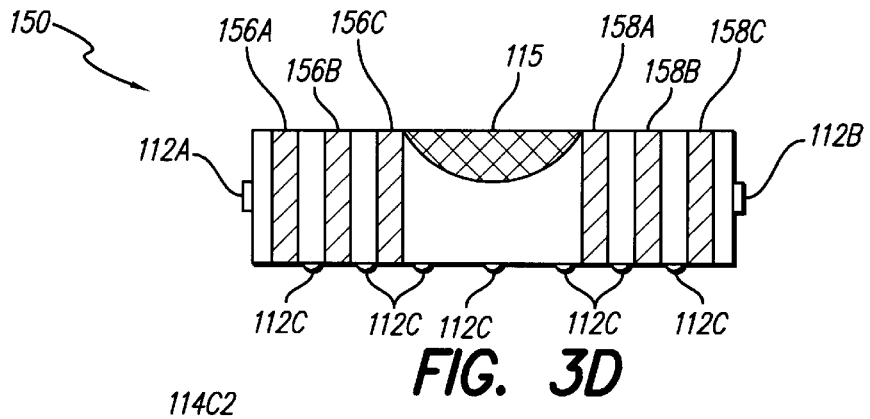
FIG. 3D is a side view of another configuration of a microstimulator.
Figure 3G:
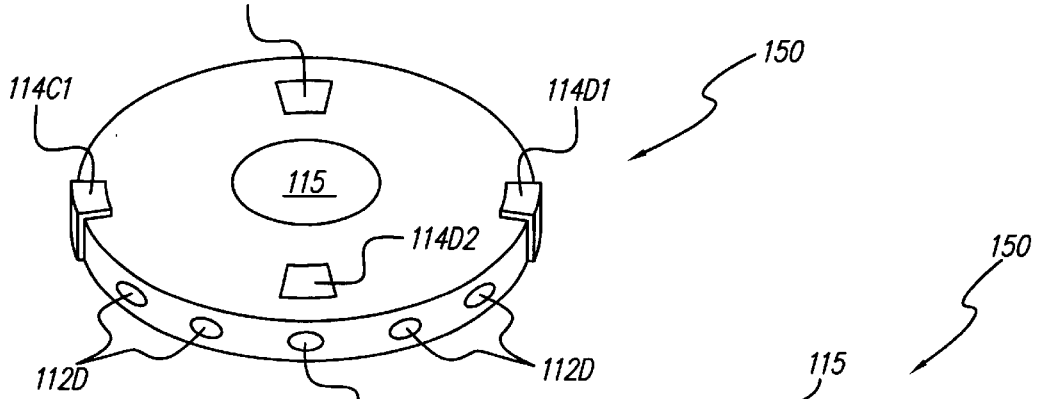
FIG. 3G is a perspective view of a pancake-shaped configuration of a microstimulator device made in accordance with the invention.
Figure 3H:
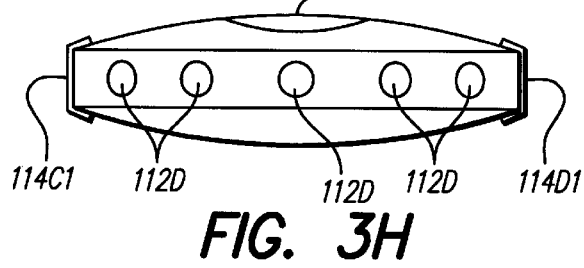
FIG. 3H is a side view of the pancake-shaped configuration of FIG. 3G.
Figure 3I:
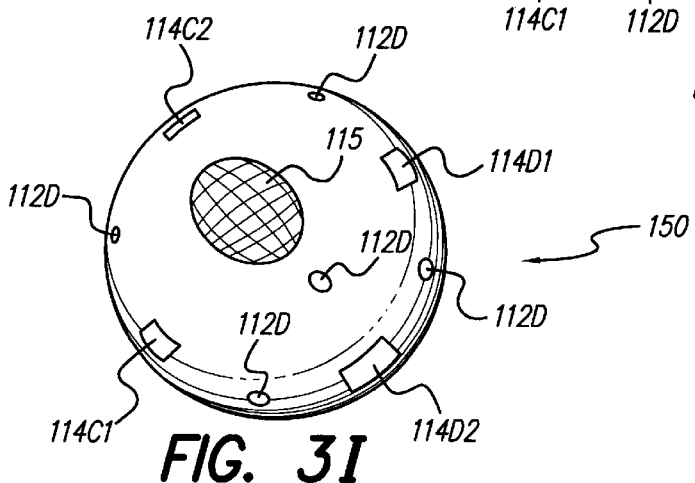
FIG. 3I is a perspective view of a spherical-shaped configuration of a microstimulator device made in accordance with the invention.

The number and orientation of electrodes present on stimulator 150 may also be varied. For example, and as mentioned earlier, a thin cylindrical microstimulator may have an anode at one end and a cathode at the other (FIGS. 3A and 3B). As another example and as depicted in FIG. 3D, a thin cylindrical microstimulator may have a plurality of anodes 156A, 156B, 156C and/or cathodes 158A, 158B, 158C distributed along its surface. According to yet another example, a relatively flat circular (i.e., pancake-shaped or disk-shaped) stimulator device (FIGS. 3G and 3H) or a substantially spherical device (FIG. 3I) may have a plurality of anodes and/or cathodes distributed along its surface and periphery. For example, and as shown in FIGS. 3G, 3H, and 3I, a stimulator 150 may have infusion outlet(s) 112D and/or electrodes 114C, 114D distributed around its periphery, such as a plurality of anodes 14C1, 14C2 and/or cathodes 14D1, 14D2 distributed along the surface and periphery of a device.

In certain embodiments of the instant invention, microstimulator 150 comprises two, leadless electrodes. However, either or both electrodes 156 and 158 (or any of the electrodes, when more than two are used) may alternatively be located at the distal portion of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the implantable stimulator 150, while allowing most elements of stimulator 150 to be located in a more surgically convenient site. This minimizes the distance traversed and the surgical planes crossed by the device and any lead(s). In most uses of this invention, the leads are no longer than about 150 mm, so that stimulator 150, including leads and electrodes, is contained entirely within neoplasm 108, or is located nearby. As described herein, placement entirely within or near a neoplasm includes placement of a microstimulator with, for instance, an anode located in the neoplasm, while a cathode (which electrode may be the microstimulator capsule itself) is located outside but close to the neoplasm, and includes placement of all electrodes within the neoplasm while the bulk of the microstimulator is outside but close to the neoplasm, and also includes placement of an infusion outlet within the neoplasm while one or more electrodes are outside but close to the neoplasm, and other similar arrangements that provide the benefits of the disclosed therapy.

In addition, the length and/or shape of the microstimulator may be varied in order to deliver more effective treatment, e.g., to treat neoplasms of different shapes and sizes. For example, if the microstimulator is a thin cylindrical device with an electrode at each end, the length of this device may be varied to treat neoplasms of different sizes or shapes. As another example, if the microstimulator is a flat circular (i.e., pancake-shaped) stimulator device with electrodes distributed around its periphery, the diameter of this device may be varied to treat neoplasms of different sizes. As yet another example, the size and configuration of a substantially spherical device may be varied to treat different sizes of neoplasm.

Microstimulator(s) 150, when certain configurations are used, may be implanted with a surgical tool such as a tool specially designed for the purpose, or may be placed, for instance, via a small incision and through a small cannula. Alternatively, device(s) 150 may be implanted via conventional surgical methods, or may be implanted using other endoscopic or laparoscopic techniques. A more complicated surgical procedure may be required for sufficient access to certain tissue, for fixing the microstimulator in place, and/or when implanting microstimulators of certain shapes.

The external surfaces of stimulator 150 may advantageously be composed of biocompatible materials. Capsule 152 may be made of, for instance, glass, ceramic, or other material that provides a hermetic package that will exclude water vapor but permit passage of electromagnetic fields used to transmit data and/or power. Electrodes 156 and 158 may be made of a noble or refractory metal or compound, such as platinum, iridium, tantalum, titanium, titanium nitride, niobium, or alloys of any of these, in order to avoid corrosion or electrolysis which could damage the surrounding tissues and/or the device.

Figure 4A:
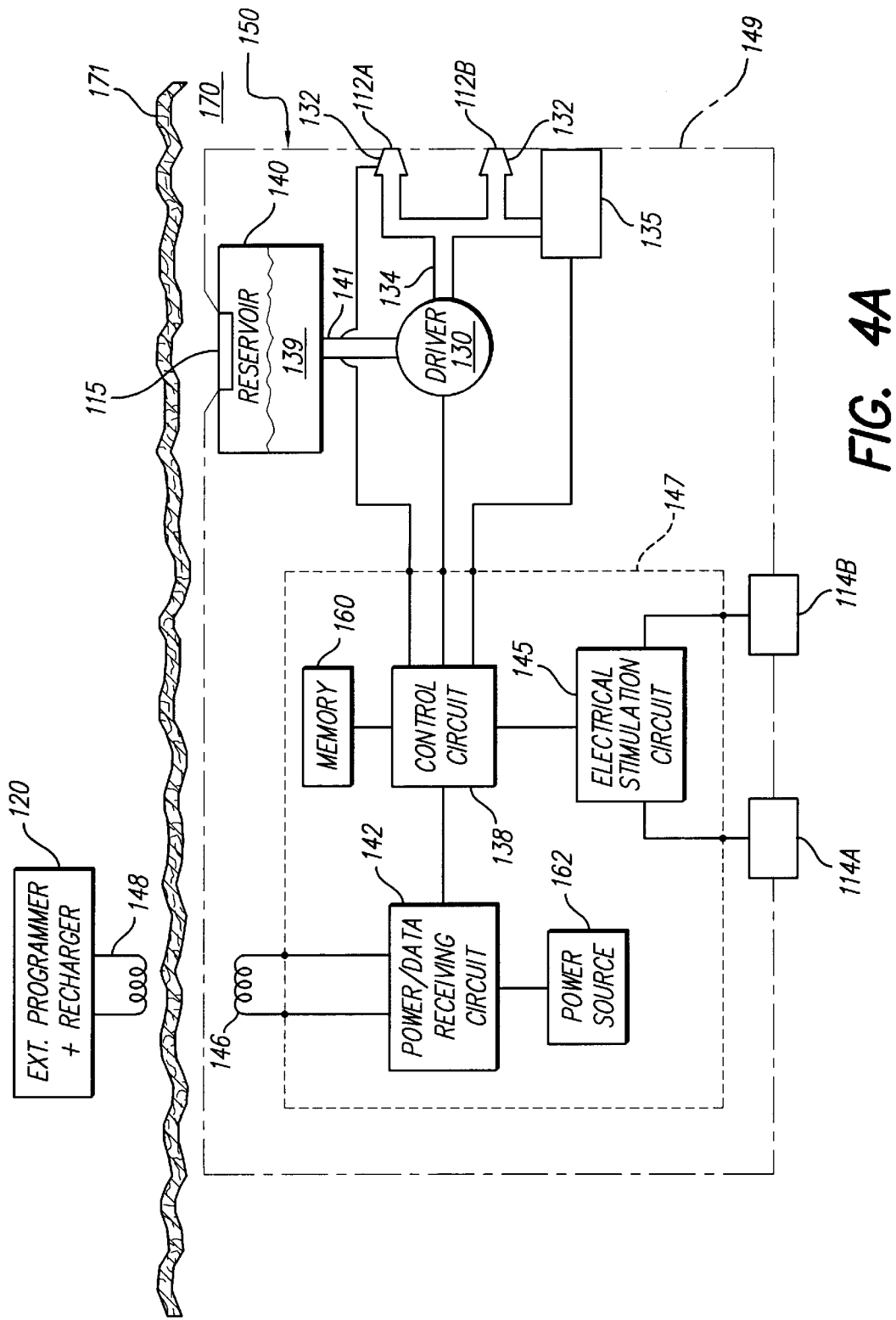
FIG. 4A is a functional block diagram of a microstimulator device made in accordance with the invention that includes both electrical and drug stimulation capabilities.

As seen best in FIG. 4A, some configurations of microstimulator 150 include a reservoir(s) 140 that contains a fluid(s) 139 that may consists of and/or contains a drug(s) to be delivered to a patient. Reservoir 140 is typically impermeable to the substances it contains. The reservoir may be relatively stiff or may be flexible, e.g., a flexible bag-type reservoir or a deformable bellows.

Figure 4B:
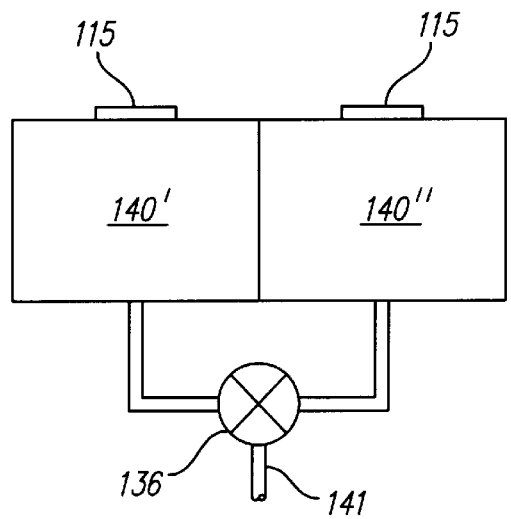
FIG. 4B schematically depicts a configuration of a reservoir used within the device of FIG. 4A.

In some embodiments, as shown in FIG. 4B, microstimulator 150 further includes a fluid mixer 136 for mixing fluids that are contained within multiple isolated reservoirs 140', 140" prior to delivery to the patient. Means of refilling, e.g., septa 115, allow access to reservoirs 140', 140". While only two isolated reservoirs 140' and 140" are shown in FIG. 4B, such is only exemplary, and any number of isolated reservoirs could be used. Such mixer 136 allows, for instance, delivery of substances that are otherwise too volatile to be stored within the patient for days or months, and also provides an additional safety mechanism in that an inert substance may be delivered should the device suffer a breach of a single reservoir.

As shown in FIG. 4A, possible configurations also include a driver 130 for driving a fluid(s) out infusion outlet(s) 112A, 112B in the device. Driver 130 may be a peristaltic pump, diaphragmatic pump, may be actuated by electrostatic and/or electromagnetic means, may be a solenoid-activated negative pressure pump, a positive pressure pump used in combination with an accumulator pump, or any other useful means known in the art. Such driver 130 may also incorporate redundant or fail-safe valves together with sensor/shutdown circuits to prevent accidental delivery of the fluid(s) contained in the reservoir. Infusion outlets 112A and 112B are in fluid communication with driver 130, e.g., via tubing or channels 134. Driver 130 may be adjusted by control circuitry 138 internal to the device, e.g., based on a desired time-infusion rate profile. Alternatively or additionally, driver 130 may be adjusted by one or more external devices 120, such as a sensor device or a remote control, which external device(s) 120 may communicate with stimulator 150 via an inductive coil 148 or the like, as described herein.

As seen in FIG. 4A, various configurations also include a regulator(s) 132 for regulating or restricting flow. As with driver 130, regulator 132 may be adjusted by control circuitry 138 internal to the device and/or by an external device 120. Regulator(s) 132 may, for example, comprise a capillary tube(s), a mechanically, electrostatically, and/or electromagnetically actuated mechanical valves(s) that adjusts the size of a lumen of an infusion outlet or a catheter, or a number of multi-stable valves, such as shape-memory valves or micro-machined valves, as known to those skilled in the art. Regulator 132 may alternatively or additionally include a pressure responsive control valve for connecting a secondary regulator, such as an additional capillary tube(s), in series with the baseline flow path to prevent any undesired infusion rate changes, e.g., if the patient encounters a high altitude ambient pressure.

Microstimulator 150 may also include a non-occlusion device 135 for ensuring that fluid egress is not occluded or that it may be cleared if occluded, e.g., by tissue or debris from a patient's body. Such non-occlusion device 135 typically includes a mechanical device, such as a wiper or a plunger, that periodically or episodically clears an occluded lumen. Non-occlusion device 135 may alternatively or additionally include an electrical pulse(s) or other electrical signal that may disintegrate an occlusion, and/or device 135 may compress or expand the infusion outlet(s) such that the occlusion is broken down or is otherwise allowed to escape, and/or device 135 may include the application of high fluid pressure behind the occlusion to force it out of the infusion outlet(s), and/or device 135 may include a filter over the infusion outlet. The stimulator may trigger the non-occlusion device upon sensing that an occlusion is present, e.g., through detection of increased pressure in driver 130 or regulator 132.

The dashed line 147 shown in FIG. 4A represents the boundaries of an exemplary hermetically-sealed case in which a control circuit 138, a power/data receiving circuit 142, electrical stimulation circuit 145 such as pulse or current generator circuitry, memory 160, and power source/ storage 162 are housed. The large heavy dots on line 147 represent electrical feed-through connectors that allow electrical access into hermetically-sealed case 147. The dashed-dotted line 149 represents the boundaries of the entire microstimulator 150, which contains other elements which may not necessarily be included within the hermetically-sealed portion 147. These elements include, e.g., an inductive coil 146 or the like for receiving and/or transmitting RF data and/or power (for instance, with inductive coils 148 or by other means of communication, such as an RF transmitter and receiver), a pump or other driver 130, a reservoir 140 for holding fluid 139 (e.g., a drug), tubing 141 (if necessary) connecting reservoir 140 with driver 130, tubing 134 (if necessary) connecting driver 130 with regulator 132 and/or non-occluding device 135, which non-occluding device 135 keeps tubing 134, regulator 132, and outlets 112A, 112B free from occlusions. Depending upon the type of driver 130 used, portions thereof (e.g., electronic control circuits and/or elements) may also be included within the hermetically-sealed portion 147 of stimulator 150.

Microstimulator 150 contains, when necessary and/or desired, a power/data receiving circuit 142 for receiving data and/or power from outside the body by inductive, radio frequency (RF), or other electromagnetic coupling. In some embodiments, electrical circuitry 154 includes the power/data receiving circuit 142 and an inductive coil 146 or other means for receiving and transmitting RF data and/or power, control circuit 138 and electrical stimulation circuit 145, including an integrated circuit (IC) chip for decoding and storing stimulation parameters and generating stimulation current/pulses (either intermittent or continuous) to be delivered via electrodes 114A and 114B, and additional discrete electronic components required to complete the electronic circuit functions, e.g. capacitor(s), resistor(s), coil(s), and the like.

Microstimulator 150 also includes, when necessary and/or desired, a programmable memory 160 for storing set(s) of data, stimulation, control parameters, and/or other data, if required. Among other things, memory 160 may allow electrical stimulation, drug stimulation, and/or control parameters to be adjusted to settings that are safe and efficacious with minimal discomfort for each individual. Specific parameters may provide therapeutic advantages for various stages and forms of cancer/neoplastic disease. In addition, different parameters may have different effects on different tissue. For instance, stimulation and control parameters may be chosen to target specific tissues and to exclude others. For example, relatively higher current amplitudes may affect a larger volume of tissue around an electrode.

The volume of tissue necrosis is likely to increase with an increasing amount of electric current or charge (due to increased production of reactive species) or with an increasing electric field (due to increased cell membrane permeability) delivered to the tissue. As another example, electric currents applied at different frequencies and/or with different chemotherapy agents and/or immunotherapy agents may have different effects on different tissues. For example, certain chemotherapy and/or immunotherapy agents may preferentially affect certain tissues. For example, cyclophosphamide preferentially kills white blood cells and may thus be used as part of an electrochemotherapy regimen for treatment of leukemia and/or lymphoma. As another example, some patients may respond favorably to intermittent stimulation, while others may require continuous stimulation to alleviate their symptoms.

As yet another example, direct electric currents are also likely to have different effects than pulsatile or periodic waveforms. For example, direct electric currents are significantly more toxic than charge-balanced biphasic periodic waveforms typically used in neurostimulation. As another example, biphasic periodic waveforms are also likely to have different effects than monophasic periodic waveforms. For example, decades ago, research demonstrated that monophasic waveforms are toxic to neurons, due to the build-up of charge and associated pH change in the neurons. Since then, to avoid destroying neurons, biphasic pulses have been used, because the second phase reverses the charge injection and effectively removes the charge from the neuron. As an example from direct electric current therapy, a relatively lower amplitude direct electric current applied over a relatively longer treatment period may be more effective than a relatively higher amplitude direct electric current applied over a relatively shorter treatment period, even if the two treatments deliver the same amount of charge to the tissue. These effects may still apply when applied together with some chemotherapy agents, and the opposite effect may occur with other chemotherapy agents.

Different drug stimulation parameters may also have different effects on neoplastic tissue. For instance, different chemotherapy agents or other medications may be delivered at differing rates or with differing schedules. As another example, a relatively low infusion rate applied over a relatively long treatment period may be more effective than a relatively high infusion rate applied over a relatively short treatment period, even if the two treatments deliver the same amount of drug(s) to the tissue.

In addition, different combinations of synchronized electrical and drug stimulation parameters may have different effects on neoplastic tissue. For instance, some chemotherapy agents may be potentiated by a relatively low amplitude electrical stimulus applied for a relatively long time following administration, while other chemotherapy agents may be potentiated by a relatively high amplitude electrical stimulus applied for a relatively short time following administration. As another example, some combinations of electrical stimulation and chemotherapy may be appropriately applied at a steady basal rate, perhaps with periodic bolus dosing. However, it may not be necessary or desired to synchronize the electrical and drug stimulation treatments. For instance, in some cases, the best results may be achieved by applying continuous electrical stimulation while continuously releasing a chemotherapy agent.

Thus, according to certain embodiments of the invention, the chemotherapy agent(s) are administered systemically, and the microstimulator is activated at the same time or a predetermined time thereafter (e.g., ten minutes) to produce electrical stimulation. The microstimulator may continue to provide electrical stimulation for a predetermined period following the administration of the chemotherapy agent(s), e.g., 2 hours. This may provide benefits for patients, such as continuing to cause selective uptake of chemotherapy agents even after administration has ceased, and/or providing benefits of chemotherapy even at normally sub-therapeutic levels. According to additional embodiments of the invention, the microstimulator provides electrical stimulation continuously, and the electrical stimulation potentiates the effects of chemotherapy agents and also may also provide direct effects on cancer, e.g., direct electric current-induced cytotoxicity.

Some embodiments of implantable stimulator 150 also include a power source and/or power storage device 162. Possible power options for a stimulator device of the present invention, described in more detail below, include but are not limited to an external power source coupled to stimulator 150, e.g., via an RF link; a self-contained power source utilizing any suitable means of generation and/or storage of energy (e.g., a primary battery, a replenishable or rechargeable battery such as a lithium ion battery, an electrolytic capacitor, a super- or ultra-capacitor, or the like); and/or if the self-contained power source is replenishable or rechargeable, means of replenishing or recharging the power source (e.g., an RF link; an optical link, a thermal link, or other energy-coupling link).

Figure 5:
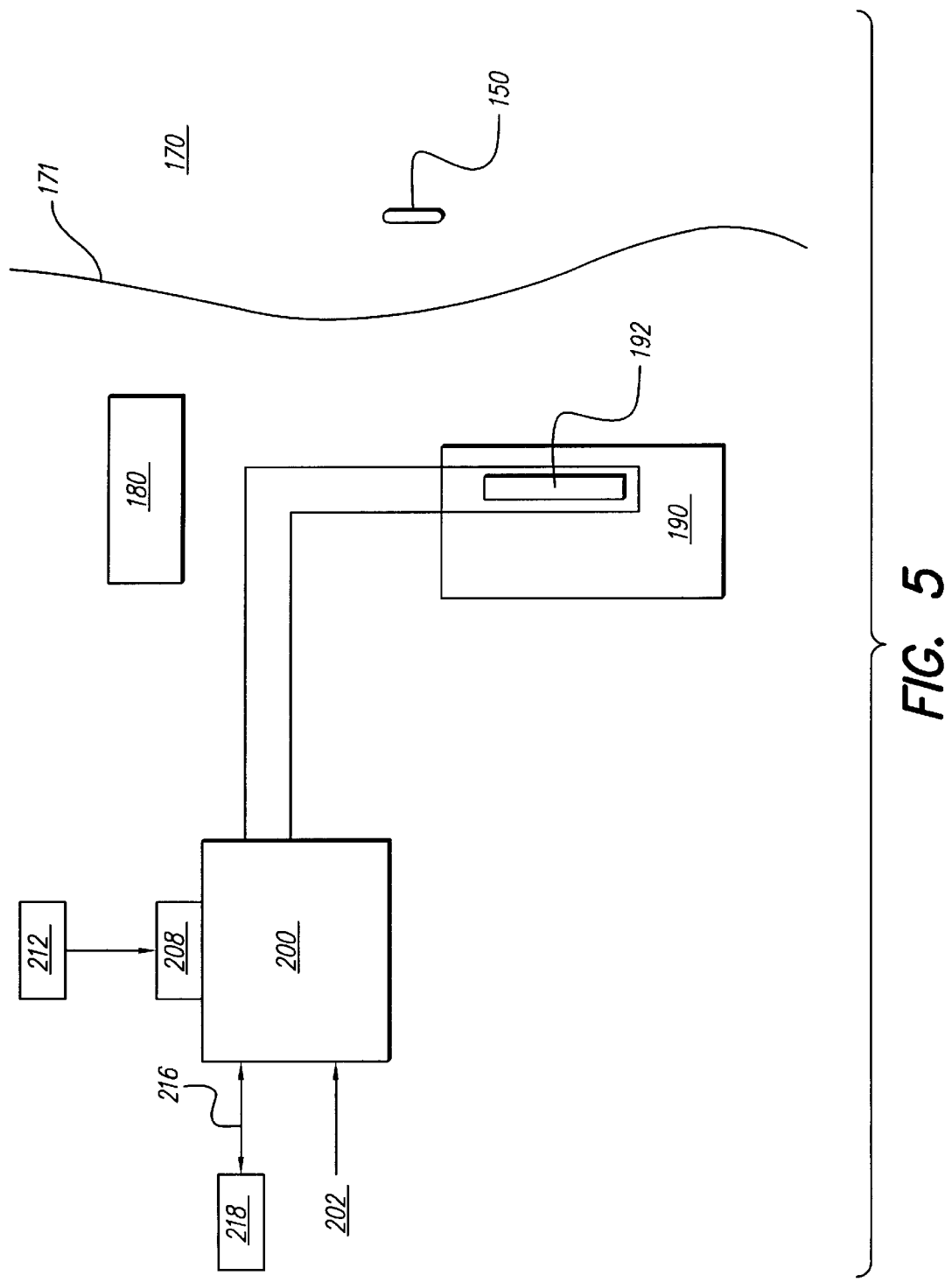
FIG. 5 illustrates additional exemplary external components of the invention.

In certain embodiments, and as illustrated in the exemplary embodiment of FIG. 5, the patient 170 switches stimulator 150 on and off by use of controller 180, which may be handheld. Controller 180 operates to control stimulator 150 by any of a variety of methods, including sensing the proximity of a permanent magnet located in controller 180, sensing RF transmissions from controller 180, or the like. Other methods for controlling microstimulator 150 are possible, such as an implanted button that may be pressed to activate stimulator 150.

The embodiment of FIG. 5 also depicts exemplary external components related to programming and providing power to implantable stimulator 150. When it is required to communicate with implanted stimulator 150, patient 170 is positioned on or near external appliance 190, which appliance contains one or more inductive coils 192 or other means of communication (e.g., RF transmitter and receiver). External appliance 190 is connected to or is a part of external electronic circuitry appliance 200 which may receive power 202 from a conventional power source. External appliance 200 contains manual input device 208, e.g., a keypad, whereby the patient 170 or a caregiver 212 may request changes in electrical and/or drug stimulation parameters produced during the normal operation of implantable stimulator 150. In these embodiments, manual input device 208 include various electro-mechanical switches and/or visual display devices that provide the patient and/or caregiver with information about the status and prior programming of implantable stimulator 150.

Alternatively or additionally, external electronic appliance 200 is provided with an interface 216 for interacting with other computing device(s) 218, such as by a serial interface cable or infrared link to a personal computer, to a telephone modem, or the like. Such interface 216 may permit a clinician to monitor the status of the implant and prescribe new stimulation parameters from a remote location.

The external appliance(s) may be embedded in a cushion, pillow, mattress cover, or garment. Other possibilities exist, including a necktie, belt, scarf, patch, or other structure(s) that may be affixed to the patient's body or clothing. External appliances may include a package that can be, e.g., worn on the belt, may include an extension to a transmission coil affixed to the body, e.g., with a velcro band or adhesive, or may be combinations of these or other structures able to perform the functions described herein.

In order to help determine the amount, type, strength, and/or duration of electrical current and/or drug infusion required to produce the desired effect, in some embodiments, a patient's response to and/or need for treatment is sensed. For example, microstimulator 150 may incorporate means of sensing tissue necrosis or byproducts thereof (e.g., via a pH sensor or impedance sensor), means of sensing tissue volume or indirect indicators thereof (e.g., via a pressure or tissue impedance sensor), and/or means of sensing tissue function or indirect indicators thereof (e.g., electromyograph or EMG). Other measures of the state of the patient may additionally or alternatively be sensed, e.g., hormone, enzyme, interleukin, cytokine, lymphokine, chemokine, growth factor, neurotransmitter, ketone, electrolyte, medication or other drug levels and/or changes in these or other substances in the blood plasma or local interstitial fluid. For instance, the level or changes in level of prostate-specific antigen (PSA), a key indicator of prostate cancer progression, may be sensed. As another example, the level or changes in level of alpha-fetoprotien (AFP), a key liver cancer tumor marker, may be sensed. Other liver cancer tumor markers may additionally or alternatively be sensed, such as alpha-L-fucosidase (AFu), gamma-glutamyltransferase (GGT), sialic acid (SA) and/or carcinoembryonic antigen (CEA). Substances may be sensed, for instance, using one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands).

A microstimulator may additionally or alternatively incorporate means of sensing electrical current levels and/or waveforms supplied by another source of electrical energy. For instance, multiple microstimulators may be placed in a patient, and one stimulator may modulate its output based on the current supplied by other microstimulators. Other methods of determining a patient's response to and/or need for treatment include an iterative process whereby the physician sets stimulation levels and then adjusts them periodically based on diagnostic imaging results and/or a patient's report of symptoms, as well as other methods mentioned herein, and yet others that will be evident to those skilled in the art upon reviewing the present disclosure.

For instance, in several embodiments of the present invention, a first and second "microstimulator" are provided. The second "microstimulator" periodically (e.g., once per minute) records pH (and/or AFP, PSA, oxygen level, impedance, pressure, or other indicator), which it transmits to the first stimulator. The first stimulator uses the sensed information to adjust electrical and/or drug stimulation parameters according to an algorithm programmed, e.g., by a physician. For example, if the pH is close to normal (e.g., approximately 7.4), then stimulation amplitude is increased. In some alternatives, one "microstimulator" performs both the sensing and stimulating functions, as discussed in more detail herein.

While a microstimulator may also incorporate means of sensing one or more conditions of the patient, it may alternatively or additionally be desirable to use a separate or specialized implantable device, such as an implantable pH sensor, to record and telemeter physiological conditions/responses in order to adjust stimulation parameters. This information may be transmitted to an external device, such as external appliance 190, or may be transmitted directly to implanted stimulator(s) 150. However, in some cases, it may not be necessary or desired to include a sensing function or device, in which case stimulation parameters may be fixed and/or determined and refined, for instance, by patient feedback, or the like.

Thus, it is seen that in accordance with the present invention, one or more external appliances may be provided to interact with microstimulator 150, and may be used to accomplish, potentially among other things, one or more of the following functions:

Function 1: If necessary, transmit electrical power from the external electronic appliance 200 via appliance 190 to stimulator 150 in order to power the device and/or recharge the power source/storage device 162. External electronic appliance 200 may include an automatic algorithm that adjusts electrical and/or drug stimulation parameters automatically whenever the implantable stimulator(s) 150 is/are recharged.

Function 2: Transmit data from the external appliance 200 via the external appliance 190 to the implantable stimulator 150 in order to change the parameters of electrical and/or drug stimulation produced by stimulator 150.

Function 3: Transmit sensed data indicating a need for treatment or in response to stimulation from microstimulator 150 (e.g., EMG, change in pH, hormone, or medication level, change in impedance or pressure, or other activity) to external appliance 200 via external appliance 190.

Function 4: Transmit data indicating state of the implantable stimulator 150 (e.g., battery level, drug level, stimulation parameters, etc.) to external appliance 200 via external appliance 190.

By way of example, a treatment modality for liver cancer may be carried out according to the following sequence of procedures:

1. A stimulator 150 is implanted so that it is entirely within neoplasm 108. If necessary or desired, one or more additional stimulator(s) 150 may be implanted in other areas of neoplasm 108, such as at a location near a major blood vessel feeding the neoplasm. In another alternative, the electrodes of a lead and/or the output portion of a catheter(s) are implanted in the neoplasm, while the bulk of the stimulator is implanted a short distance away, e.g., in the liver.

2. Using Function 2 described above (i.e., transmitting data) of external appliance 200 and external appliance 190, stimulator 150 is commanded to periodically infuse a chemotherapy agent(s) and to produce electric stimulation pulses during and for a time period after infusion.

3. Set stimulator on/off period(s) to an appropriate setting (s), e.g., one hour on followed by three hours off for both electrical and drug stimulation. As another example, set infusion for one hour on, then three hours off, while electrical stimulation is set to three hours on, then one hour off.

4. At some predefined interval, any change in pH, impedance, and/or oxygen level is sensed, for instance, by one or more electrodes 156 and 158 or sensors. These responses are converted to data and telemetered out to external electronic appliance 200 via Function 3. Alternatively, after an initial treatment period (e.g., one month), tumor size/state may be assessed by, for example, report of symptoms, ultrasound imaging, CT imaging, and/or other diagnostic imaging.

5. From the response data received at external appliance 200 from implantable stimulator 150, or from other assessment, the threshold for obtaining a response is determined and is used by a clinician acting directly 212 or by other computing device(s) 218 to transmit the desired stimulation parameters to stimulator 150 in accordance with Function 2. For instance, if neoplasm growth is seen on a CT scan image, infusion rate(s) and/or on periods may be increased, and/or electrical stimulation on period(s) may be increased.

6. To cease treatment, patient 170 employs controller 180 to turn off stimulator 150.

7. Periodically, the patient or caregiver recharges the power source/storage device 162 of implantable stimulator 150, if necessary, in accordance with Function 1 described above (i.e., transmit electrical power).

For the treatment of any of the various forms and degrees of cancer or other neoplastic disease, it may be desirable to modify or adjust the algorithmic functions performed by the implanted and/or external components, as well as the surgical approaches, in ways that would be obvious to skilled practitioners of these arts. For example, in some situations, it may be desirable to employ more than one implantable stimulator 150, each of which could be separately controlled, e.g., by a digital address. Multiple channels and/or multiple patterns of electrical and/or drug stimulation might thereby be programmed by the clinician and controlled by the patient to, for instance, stimulate larger areas of a tumor in order to maximize therapeutic efficacy.

In some embodiments, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. In some embodiments, the stimulation parameters used by stimulator(s) 150 are automatically adjusted based on the sensed information. Thus, the electrical and/or drug stimulation parameters may be adjusted in a closed-loop manner to provide stimulation tailored to the need for and/or response to the electrical and/or drug stimulation.

Figure 6:
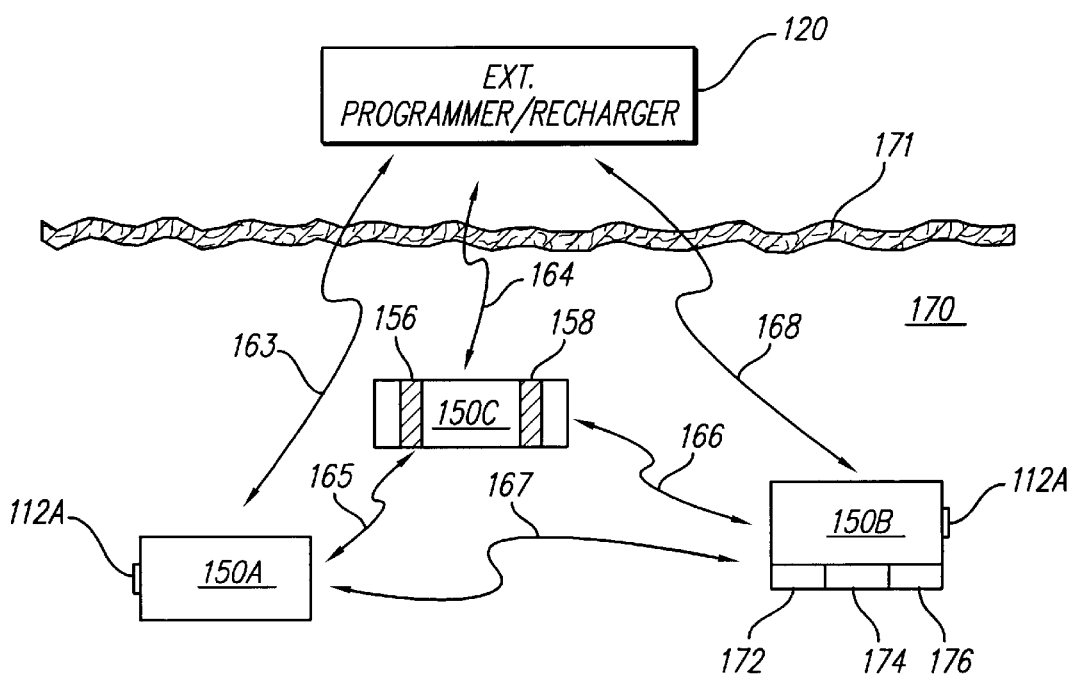
FIG. 6 depicts a system of implantable microstimulators that communicate with each other and/or with external control/programming devices.

For instance, as shown in the example of FIG. 6, microstimulator 150A, implanted beneath the skin 171 of the patient 170, provides a first medication or substance; a second implanted microstimulator 150B provides a second medication or substance; and a third implanted microstimulator 150C provides electrical stimulation via electrodes 156 and 158. As mentioned earlier, the implanted device(s) may operate independently or may operate in a coordinated manner with other similar implanted device(s), other implanted device(s), and/or other device(s) external to the patient's body, as shown by control lines 163, 164, 165, 166, 167, and 168 in FIG. 6. That is, in accordance with various embodiments of the invention, an external controller(s) 120 controls the operation of each implanted device (e.g., stimulators 150A, 150B and 150C). According to certain embodiments, an implanted device, e.g., stimulator 150A, may control or operate under the control of other implanted device(s), e.g., stimulator 150B and/or 150C, or device(s) external to the patient's body, e.g., controller 120. A microstimulator made in accordance with the invention may communicate with other implanted microstimulators, other implanted devices, and/or external devices, e.g., via an RF link, an ultrasonic link, a thermal link, an optical link, or the like. Specifically, as illustrated in FIG. 6, microstimulator 150A, 150B, and/or 150C, made in accordance with the invention, may communicate with an external remote control 120 (e.g., patient and/or physician programmer) that is capable of sending commands and/or data to a microstimulator(s), and that may also be capable of receiving commands and/or data from a microstimulator(s).

A stimulator made in accordance with the invention may communicate with one or more external or site-specific drug delivery devices, and, further, may have the control flexibility to synchronize and control the duration of drug delivery. The associated drug delivery device may provide a feedback signal that lets a microstimulator(s) and/or other control device know it has received and understood the command(s). Communication signals between the devices may be encoded to prevent accidental or inadvertent delivery of electrical or drug stimulation by other signals.

A microstimulator made in accordance with certain embodiments of the invention, further incorporates a first sensor 172 for sensing therapeutic effects, clinical variables, and/or other indicators of the state of the patient, such as level(s) of or change(s) in impedance, pH, oxygen level, pressure, EMG, or the like, resulting from the tumor and/or from the stimulation applied to the tumor. The device may additionally or alternatively incorporate a second sensor 174 (e.g., a CHEMFET) for sensing level(s) and/or change(s) in one or more hormones, enzymes, interleukins, cytokines, lymphokines, chemokines, growth factors, neurotransmitters, keytones, electrolytes medications or other drugs, PSA, AFP, AFu, GGT, SA, CEA, and/or other substances in the blood plasma or local interstitial fluid. The device may additionally or alternatively incorporate a third sensor 176 for sensing electrical current levels and/or waveforms supplied by another source of electrical energy. Sensed information may be used to control infusion and/or electrical parameters in a closed-loop manner, as shown by control lines 166, 167, and 165. Thus, sensor(s) may be incorporated into a device that also includes electrical and/or drug stimulation, or the sensor(s) (that may or may not include stimulation capabilities) may communicate the sensed information to another device(s) with stimulation capabilities. In a further alternative, one or more of the sensors may also be a stimulating electrode or other electrode. If necessary, the sensed information is transmitted to an external device, which may process the information and communicate the needed information to other internal devices providing stimulation, as shown by control lines 168, 164, and 163.

According to various embodiments of the invention, sensing and electrical stimulation are both incorporated into a single microstimulator. According to other embodiments of the invention, the sensing and drug stimulation are both incorporated into a single microstimulator. According to yet other embodiments of the invention, the sensing, electrical, and drug stimulation are all incorporated into a single microstimulator. According to various embodiments of the invention, the sensor(s) are incorporated into at least one "microstimulator" (that may or may not be capable of stimulating), and the sensed information is, if desired, communicated to at least one other microstimulator capable of stimulating, i.e., capable of supplying a direct electric current, electric current pulses, and/or drug stimulation. The implant circuitry 154 may, if necessary, amplify and transmit these sensed signals, which may be analog or digital. Information sensed by the sensor(s) may then by used to control the electrical, infusion, and/or control parameters of stimulator(s) 150 in a closed-loop manner.

According to certain embodiments of the invention, the microstimulator delivers electrical stimulation in the form of a direct electric current and/or a periodic waveform that locally potentiates the cytotoxic effects of a systemically and/or locally administered chemotherapy agent(s). The chemotherapy agent(s) may be delivered by the same microstimulator, another microstimulator, or any other drug delivery device. The combined electric stimulation and chemotherapy is likely to cause local tissue necrosis and consequent reduction in the volume of the neoplasm, thereby treating patients with cancer and other neoplastic diseases and/or the symptoms thereof. Locally delivered direct electric current (e.g., about 1–100 mA) and/or electric current pulses (e.g., about 1 mA–5 Amps) delivered in synchrony with systemically and/or locally administered agents, such as bleomycin, cisplatin, doxorubicin, and/or cyclophosphamide, are likely to produce such necrosis. (While tissue necrosis ultimately leads to reduction in volume of tissue, this therapy may cause short-term inflammation, edema, and/or swelling of the neoplasm, which may transiently increase the volume of the neoplasm.)

According to various embodiments of the invention, the electrical stimulation provided by the microstimulator combined with the chemotherapy agent(s) causes a reduction in the rate of growth of the neoplasm and a consequent reduction in the rate of volume expansion of the neoplasm, thereby treating cancer and other neoplastic diseases. Locally delivered direct electric current (e.g., about 1–100 mA) and/or electric current pulses (e.g., about 1 mA–5 Amps) delivered in synchrony with systemically and/or locally administered agents, such as bleomycin, cisplatin, doxorubicin, and/or cyclophosphamide, are likely to produce such a decrease in growth rate.

Additionally, sensor(s) described earlier may be used to orchestrate first the activation of microstimulator(s) targeting one area of the tumor, and then, when appropriate, the microstimulator(s) targeting the same or another area of the tumor, in order to control symptoms, for instance, by a different means. Alternatively, this orchestration may be programmed, and not based on a sensed condition.

While the invention herein disclosed has been described by way of specific embodiments and applications thereof, numerous modifications and variations could be made thereto by those skilled in the art without departing from the scope of the invention set forth in the claims.

What is claimed is:

1. A method for treating a patient with neoplastic disease, comprising:

providing at least one stimulator having at least two electrodes and at least one reservoir and at least one infusion outlet in fluid communication with the reservoir;

implanting the at least one stimulator in a neoplasm;

containing at least one drug in the at least one reservoir;

providing operating power to the at least one stimulator;

providing stimulation parameters to the at least one stimulator;

delivering the at least one drug via the at least one infusion outlet in accordance with the stimulation parameters to neoplastic tissue near the at least one stimulator; and delivering electrical stimulation in accordance with the stimulation parameters to the neoplastic tissue near the at least one stimulator;

wherein the at least one stimulator has a size and shape suitable for placement entirely within the neoplasm; and wherein the at least one drug is delivered systemically.

2. The method of claim 1 wherein the electrical stimulation delivered to the neoplastic tissue is direct electric current delivered at between about 1 mA and about 1 Amp.

3. The method of claim 1 wherein the electrical stimulation delivered to the neoplastic tissue is electrical current pulses delivered at between about 1 mA and about 5 Amps.

4. The method of claim 1 wherein the at least one drug delivered to the neoplastic tissue is at least one of bleomycin, cisplatin, doxorubicin, and cyclophosphamide.

5. The method of claim 1 further comprising
providing at least one sensor;
using the at least one sensor to sense at least one physical condition; and
providing the stimulation parameters based at least in part upon the at least one sensed condition.

6. The method of claim 5 wherein the sensed physical condition includes at least one of tissue necrosis, tissue volume, pressure, oxygen level, impedance, neurotransmitter level, change in neurotransmitter level, pH level, pH level change, hormone level, hormone level change, hormone therapy agent level, change in hormone therapy agent level, anesthetic agent level, change in anesthetic agent level, enzyme level, change in enzyme level, ketone level, change in ketone level, electrolyte level, change in electrolyte level, interleukin level, change in interleukin level, cytokine level, change in cytokine level, lymphokine level, change in lymphokine level, chemokine level, change in chemokine level, growth factor level, change in growth factor level, medication level, medication level change, chemotherapy agent level, change in chemotherapy agent level, immunotherapy agent level, change in immunotherapy agent level, level of PSA, change in PSA level, level of AFP, change in AFP level, level of AFu, change in AFu level, level of GGT, change in GGT level, level of SA, change in SA level, level of CEA, change in CEA level, EMG, level of a blood-borne substance, change in the level of a blood-borne substance, level of a local interstitial fluid, and change in the level of a local interstitial fluid.

7. The method of claim 5 wherein the at least one sensor is a part of the stimulator.

8. The method of claim 1 further comprising providing and implanting more than one stimulator.

9. A method for treating a patient with neoplastic disease, comprising:
providing at least one stimulator having at least two electrodes and at least one reservoir and at least one infusion outlet in fluid communication with the reservoir;
implanting at least one electrode and at least one infusion outlet in a neoplasm;
containing at least one drug in the at least one reservoir;
providing operating power to the at least one stimulator;
providing stimulation parameters to the at least one stimulator;
delivering the at least one drug via the at least one infusion outlet in accordance with the stimulaton parameters to neoplastic tissue near the at least one infusion outlet; and
delivering electrical stimulation in accordance with the stimulation parameters to the neoplastic tissue near the at least two electrodes;
wherein the at least one stimulator has a size and shape suitable for placement entirely within or near the neoplasm.

10. The method of claim 9, further comprising:
providing at least one sensor;
using the sensor to sense a physical condition; and
determining the stimulation parameters based at least in part upon the sensed condition.

11. The method of claim 10 wherein the at least one sensor is a part of the stimulator.

12. The method of claim 10 wherein the sensed physical condition includes at least one of tissue necrosis, tissue volume, pressure, oxygen level, impedance, neurotransmitter level, change in neurotransmitter level, pH level, pH level change, hormone level, hormone level change, hormone therapy agent level, change in hormone therapy agent level, anesthetic agent level, change in anesthetic agent level, enzyme level, change in enzyme level, ketone level, change in ketone level, electrolyte level, change in electrolyte level, interleukin level, change in interleukin level, cytokine level, change in cytokine level, lymphokine level, change in lymphokine level, chemokine level, change in chemokine level, growth factor level, change in growth factor level, medication level, medication level change, chemotherapy agent level, change in chemotherapy agent level, immunotherapy agent level, change in immunotherapy agent level, level of PSA, change in PSA level, level of AFP, change in AFP level, level of AFu, change in AFu level, level of GGT, change in GGT level, level of SA, change in SA level, level of CEA, change in CEA level, EMG, level of a blood-borne substance, change in the level of a blood-borne substance, level of a local interstitial fluid, and change in the level of a local interstitial fluid.

13. The method of claim 9 further comprising providing and implanting more than one stimulator.

14. A method for treating a patient with neoplastic disease, comprising:
providing at least one stimulator having at least two electrodes;
implanting at least one electrode in a neoplasm;
providing operating power to the at least one stimulator;
providing stimulation parameters to the at least one stimulator;
providing at least one cytotoxic drug;
delivering the at least one drug to the neoplasm; and
delivering electrical stimulation in accordance with the stimulation parameters to the neoplastic tissue near the at least two electrodes;
wherein the at least one stimulator has a size and shape suitable for placement entirely within or near the neoplasm; and
wherein the at least one drug is delivered systemically.

15. The method of claim 14 wherein the at least one drug is also delivered locally.

16. The method of claim 14 wherein the electrical stimulation delivered to the neoplastic tissue is direct electric current delivered at between about 1 mA and about 1 Amp.

17. The method of claim 14 wherein the electrical stimulation delivered to the neoplastic tissue is electrical current pulses delivered at between about 1 mA and about 5 Amps.

18. The method of claim 14 wherein the at least one drug delivered to the neoplasm is at least one of bleomycin, cisplatin, doxorubicin, and cyclophosphamide.

19. The method of claim 14 further comprising
providing at least one sensor;
using the at least one sensor to sense at least one physical condition; and
providing the stimulation parameters based at least in part upon the at least one sensed condition.

20. The method of claim 14 wherein the stimulation parameters are fixed.

* * * * *